United States Patent
Tujula et al.

(10) Patent No.: US 9,328,726 B2
(45) Date of Patent: May 3, 2016

(54) SLIDING GUIDE FOR A PERISTALTIC PUMP

(75) Inventors: Anssi Tujula, Vainikkala (FI); Markus Rossi, Joutseno (FI)

(73) Assignee: FLOWROX OY, Lappeenranta (FI)

( * ) Notice: Subject to any disclaimer, the term of this patent is extended or adjusted under 35 U.S.C. 154(b) by 0 days.

(21) Appl. No.: 14/391,130

(22) PCT Filed: Apr. 16, 2012

(86) PCT No.: PCT/FI2012/050372
§ 371 (c)(1),
(2), (4) Date: Oct. 7, 2014

(87) PCT Pub. No.: WO2013/156661
PCT Pub. Date: Oct. 24, 2013

(65) Prior Publication Data
US 2015/0078941 A1 Mar. 19, 2015

(51) Int. Cl.
*F04B 43/12* (2006.01)
*A61M 5/142* (2006.01)

(52) U.S. Cl.
CPC ........ *F04B 43/1276* (2013.01); *A61M 5/14232* (2013.01); *F04B 43/1238* (2013.01); *F04B 43/1261* (2013.01); *F04B 43/1284* (2013.01)

(58) Field of Classification Search
CPC .. F04B 43/012; F04B 43/123; F04B 43/1238; F04B 43/1253; F04B 43/1276; F04B 45/08
USPC .......... 417/474, 476, 477.8, 477.11; 604/6.11
See application file for complete search history.

(56) References Cited

U.S. PATENT DOCUMENTS

| | | | |
|---|---|---|---|
| 460,944 A * | 10/1891 | Burson | .................... F04B 45/08 417/477.8 |
| 4,214,855 A * | 7/1980 | Gerritsen | .................... 417/477.8 |
| 7,726,956 B2 | 6/2010 | Riihimäki | |
| 2002/0173755 A1 * | 11/2002 | Christenson | ...... A61M 5/14232 604/288.04 |
| 2003/0021710 A1 * | 1/2003 | Miyazawa | .......... F04B 43/1253 417/477.11 |
| 2005/0053502 A1 * | 3/2005 | Souza | .................. B41J 2/17596 417/477.11 |
| 2006/0110275 A1 * | 5/2006 | Riihimaki | ................... 417/477.8 |
| 2010/0129247 A1 | 5/2010 | Lauer | |

FOREIGN PATENT DOCUMENTS

| | | | | |
|---|---|---|---|---|
| DE | 3326785 A1 * | 2/1985 | .......... | F04B 43/1276 |
| DE | 4041978 A1 * | 6/1992 | .......... | F04B 43/1238 |

OTHER PUBLICATIONS

International Search Report issued in International Patent Application No. PCT/FI2012/050372 dated Dec. 10, 2012.

* cited by examiner

*Primary Examiner* — Patrick Hamo
(74) *Attorney, Agent, or Firm* — Oliff PLC

(57) ABSTRACT

A peristaltic pump that includes an assembly including a rotor configured to compress a hose/tube being positioned on a pump cavity inner perimeter and an adjustment mechanism configured to adjust the compression force imposed on the hose/tube. The adjustment mechanism includes a gear unit and a counterpart for the gear unit. The counterpart is operatively coupled to the rotor, wherein the gear unit in cooperation with the counterpart is configured to adjust a gap between the rotor outer surface and the pump cavity inner perimeter. The assembly is fixed to a sliding guide that is configured to support the hose/tube.

4 Claims, 5 Drawing Sheets

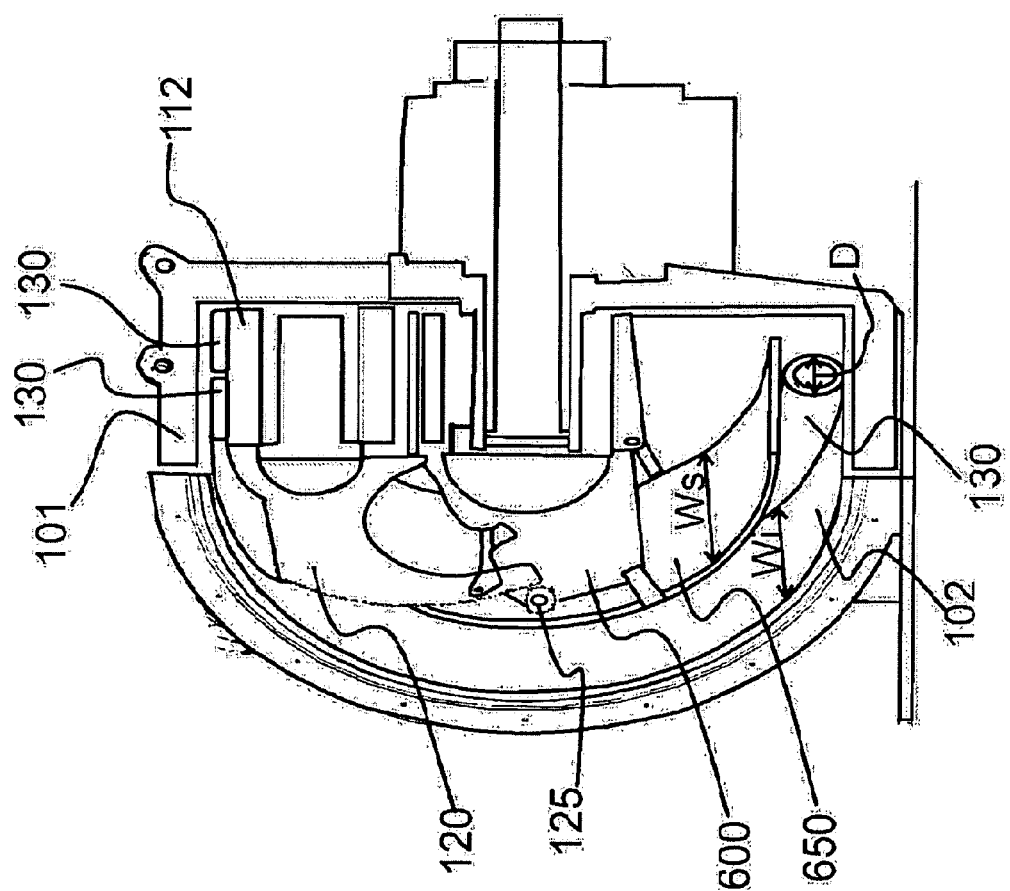

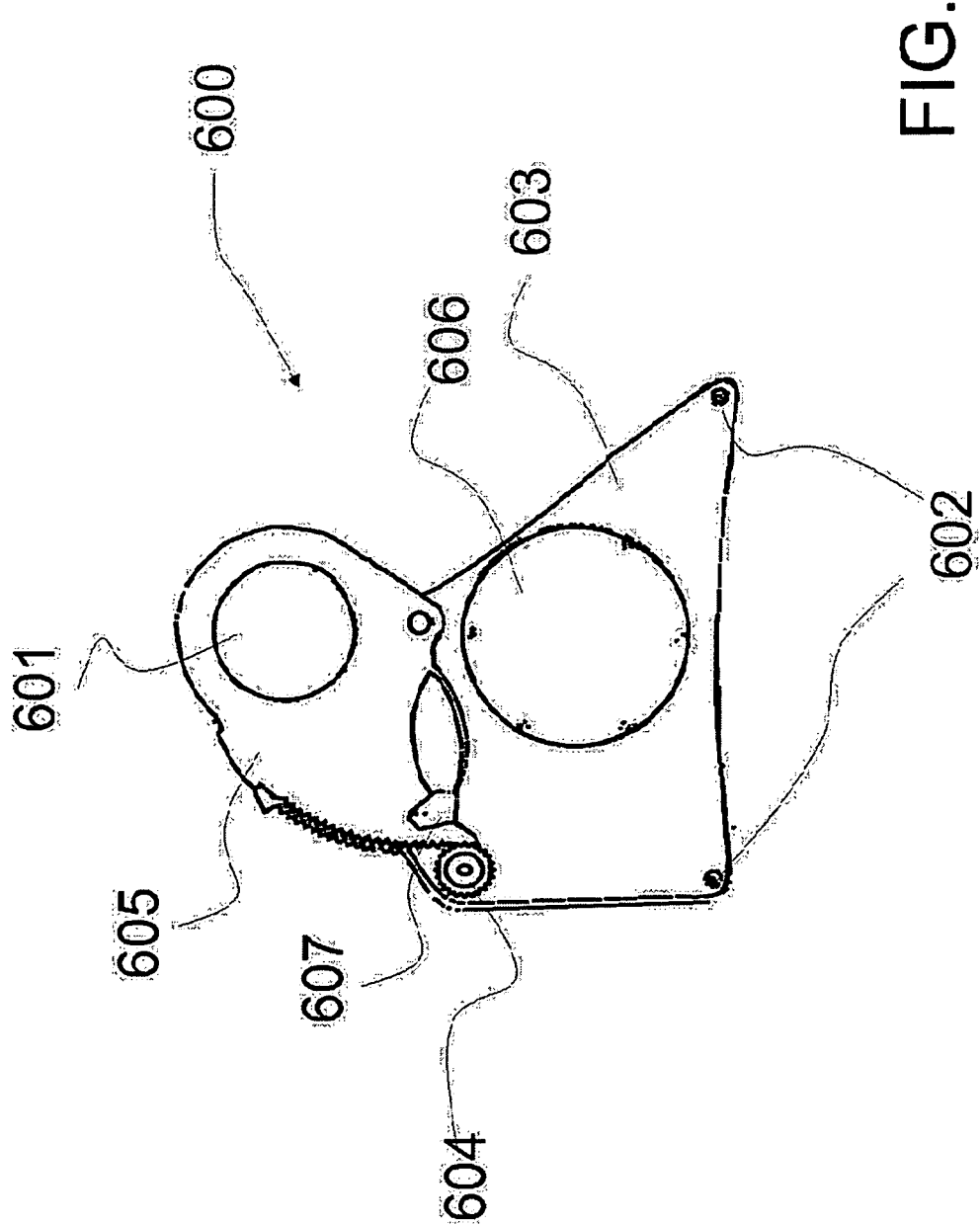

SLIDING GUIDE FOR A PERISTALTIC PUMP

CROSS REFERENCE TO RELATED APPLICATIONS

This is a National Phase of International Application No. PCT/FI2012/050372, filed Apr. 16, 2012.

FIELD OF THE INVENTION

This invention relates generally to peristaltic pumps and particularly to a solution for supporting a hose in the peristaltic pump.

BACKGROUND OF THE INVENTION

Positive displacement pumps, in which peristaltic pumps form a subclass, are employed for pumping problematic substances in particular, such as abrasive, corrosive, slurried or high-viscosity liquids and liquid-suspended solids. Peristaltic pumps are also preferred when pumping as a primary function must be complemented with accurate metering, high hygienic standard and leakproofness. Peristaltic pumps are used widely e.g. in the manufacture of foodstuffs, drugs, oil and chemical products. In heavy industries, peristaltic pumps serve to pump, inter alia, such materials as liquids and ore/mineral suspensions.

To operate properly, a peristaltic pump must be capable of forcing a volume of a fluid medium to move along a hose/tube by way of peristaltically compressing the hose from end to end during one turn of the pump rotor while simultaneously the next fluid volume is already filling the hose. Conventionally, this pumping sequence is implemented by rotating a nonrotary shoe or pressing roller, whereby the hose is subjected to progressive compression in the nip between the shoe/roller and the peripheral wall of the pump head. Furthermore, the hose/tube/tubing is selected to be sufficiently elastic and reinforces such that the hose resumes its circular profile immediately after the compression thereby creating a vacuum in its lumen thus including the entry of the next volume of the fluid medium into the hose.

SUMMARY OF THE INVENTION

The present invention is targeted to a peristaltic pump that comprises a simple and easily implementable solution for supporting the hose in the peristaltic pump.

The present application discloses a peristaltic pump and a supporting element for supporting the hose.

According to a first aspect, there is provided a peristaltic pump that comprises at least an assembly comprising at least a rotor configured to compress a hose/tube being positioned on a pump cavity inner perimeter and an adjustment mechanism configured to adjust the compression force imposed on the hose/tube, said assembly being coupled to a crankshaft of the pump body. The adjustment mechanism comprises at least of a gear unit and a counterpart for said gear unit, said counterpart being operatively coupled to said rotor, wherein the gear unit in cooperation with the counterpart are configured to adjust a gap between the rotor outer surface and the pump cavity inner perimeter, and that the assembly is fixed to a sliding guide, said sliding guide being configured to support the hose/tube.

According to an embodiment, the peristaltic pump comprises a locking means configured to function in a locking position and a rest position, where the locking means in the locking position are configured to lock the adjustment mechanism, and wherein the locking means in the rest position are configured to enable the adjusting operation of the adjusting mechanism.

According to an embodiment, the gear unit is rotatable with a crank.

According to an embodiment, the gear unit comprises a shaft and at least one gear on each end of the shaft.

According to an embodiment, the counterpart for the gear unit comprises at least one counterpart piece on each end of the rotor.

According to an embodiment, the sliding guide is arranged between the assembly and the hose to support the hose for all such length, which is not in contact with the rotor.

DESCRIPTION OF THE DRAWINGS

In the following, various embodiments of the invention will be described in more detail with reference to the appended drawings, where FIG. 4 illustrates a cross-sectional view of section A-A of the peristaltic pump comprising a sliding guide for supporting a hose, and FIG. 5 illustrates an example of a sleigh of a peristaltic pump.

DETAILED DESCRIPTION OF THE INVENTION

Figure 1:
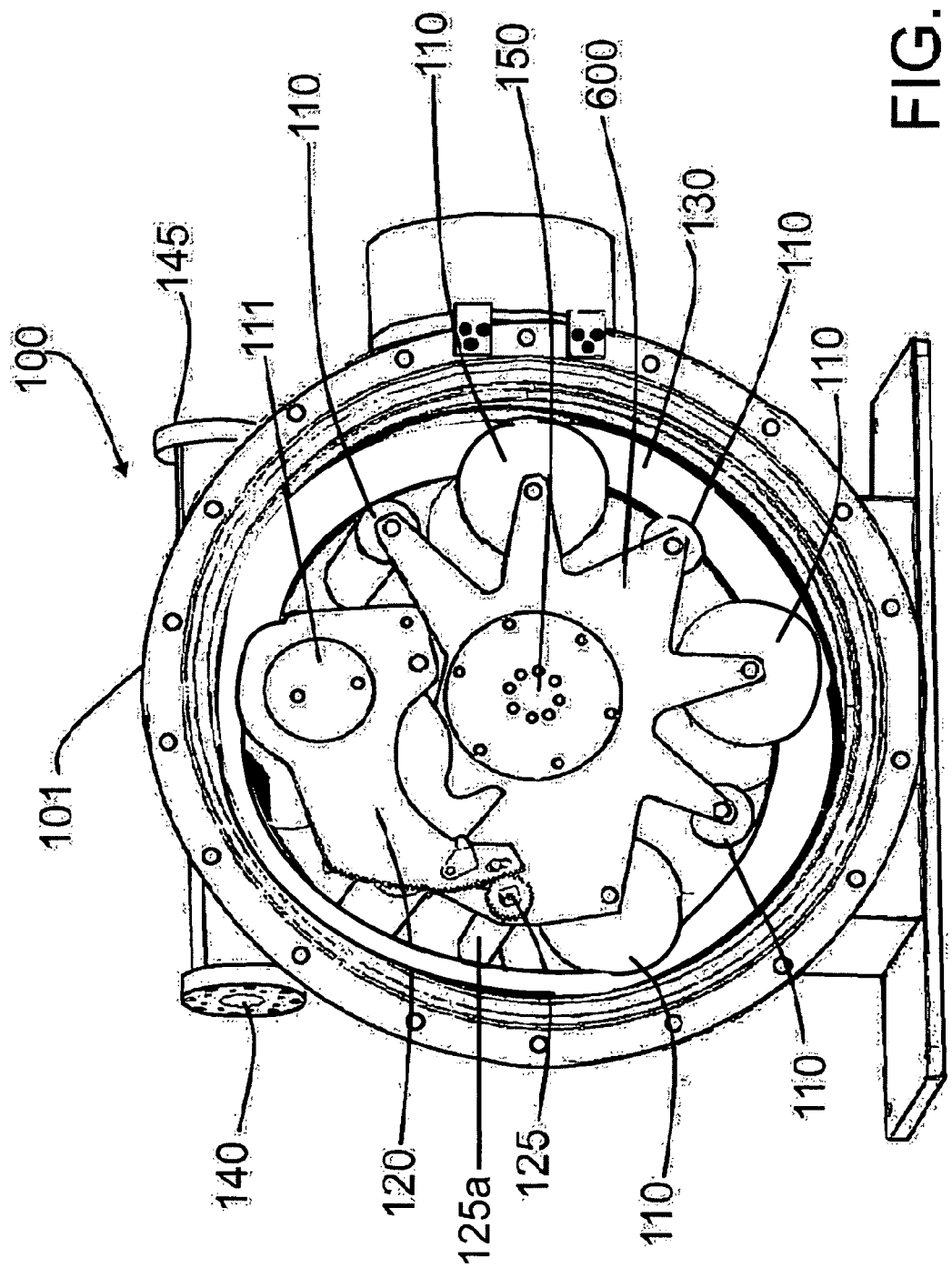
FIG. 1 illustrates an example of a peristaltic pump comprising supporting rollers for supporting a hose.

FIG. 1 illustrates an embodiment of a peristaltic hose pump comprising an adjustment mechanism. The pump 100 comprises a pump body 101, a hose 130, a rotor and feedthrough openings 140, 145 for the hose 130. The hose 130 or like elastic pump tube or pump channel is inserted into the pump cavity with a sleigh 600 housed therein, whereby the hose rests against the pump cavity inner perimeter so as to cover a full circle. The hose ends can be captively fitted in feedthrough openings 140, 145 of the pump body 101. The sleigh 600 comprises an adjustment mechanism for setting the compression applied on the pump hose 130. The rotor, the end on which is shown with reference 111, is mounted freely rotatable manner on a bearings mounted onto the sleigh 600, and the rotor is configured to function as a pressing roller of the peristaltic pump.

The adjustment mechanism serves to adjust the gap between the rotor outer surface and the pump cavity inner periphery that determines the compressive force imposed on the hose 130. The adjustment mechanism is formed at least of a gear unit 125 and a corresponding counterpart 120. The gear unit 125 may comprise at least one gear, but in this example the gear unit 125 comprises two gears on each end of a gear shaft 125a. The gear unit 125 is configured to operate with the counterpart 120, which counterpart 120 can be fixed to a shaft of the rotor 112.

The sleigh 600 is mounted on a crankshaft pin, one end of which is shown with reference numeral 150. The crankshaft is mounted freely rotatable on bearings on the rear wall of the pump body 101, centrally in regard to the pump cavity.

In use, and actuated by the drive means, the crankshaft forces the sleigh 600 to rotate in the pump cavity affecting the rotor (FIG. 4; 112) to compress the hose 130 in said pump cavity at a given distance from the interior perimeter of the pump cavity. In addition, the rotor is configured to roll on the hose surface thus propelling the bulk of substance contained in the hose 130. The distance from the interior perimeter of the pump cavity and the rotor can be defined by the adjustment mechanism and is dependent on the compression being applied to the hose 130. Hereby, the rotor compresses the hose 130 inserted in the pump cavity so that, with the rotation of the sleigh 600 and with the rolling movement of the rotor, the volume of fluid medium being pumped and contained in the hose 130 in front of the rotor is prevented from leaking in the reverse direction past the point of the hose 130 compressed by the rotor. With the rotary progressive motion of the rotor and the hose 130 recovering its circular profile immediately after the point of rotor compression, the hose 130 creates a vacuum that causes the hose 130 to become refilled with the fluid medium being pumped.

FIG. 1 also shows supporting means in the form of supporting rotors (i.e. rollers) 110 being operatively connected to the respective shoulders of the sleigh 600. The purpose of the supporting rollers 110 is to support the hose 130 so that the hose 130 maintains it circular profile and does not slacken nor knot. However, in order to have the hose supported perfectly, the peristaltic pump 100 needs to have supporting rollers 110 for all such length of the hose 130, which is not in contact with the rotor. However, the more supporting rollers the pump has, the more complex the pump configuration becomes.

Figure 2:
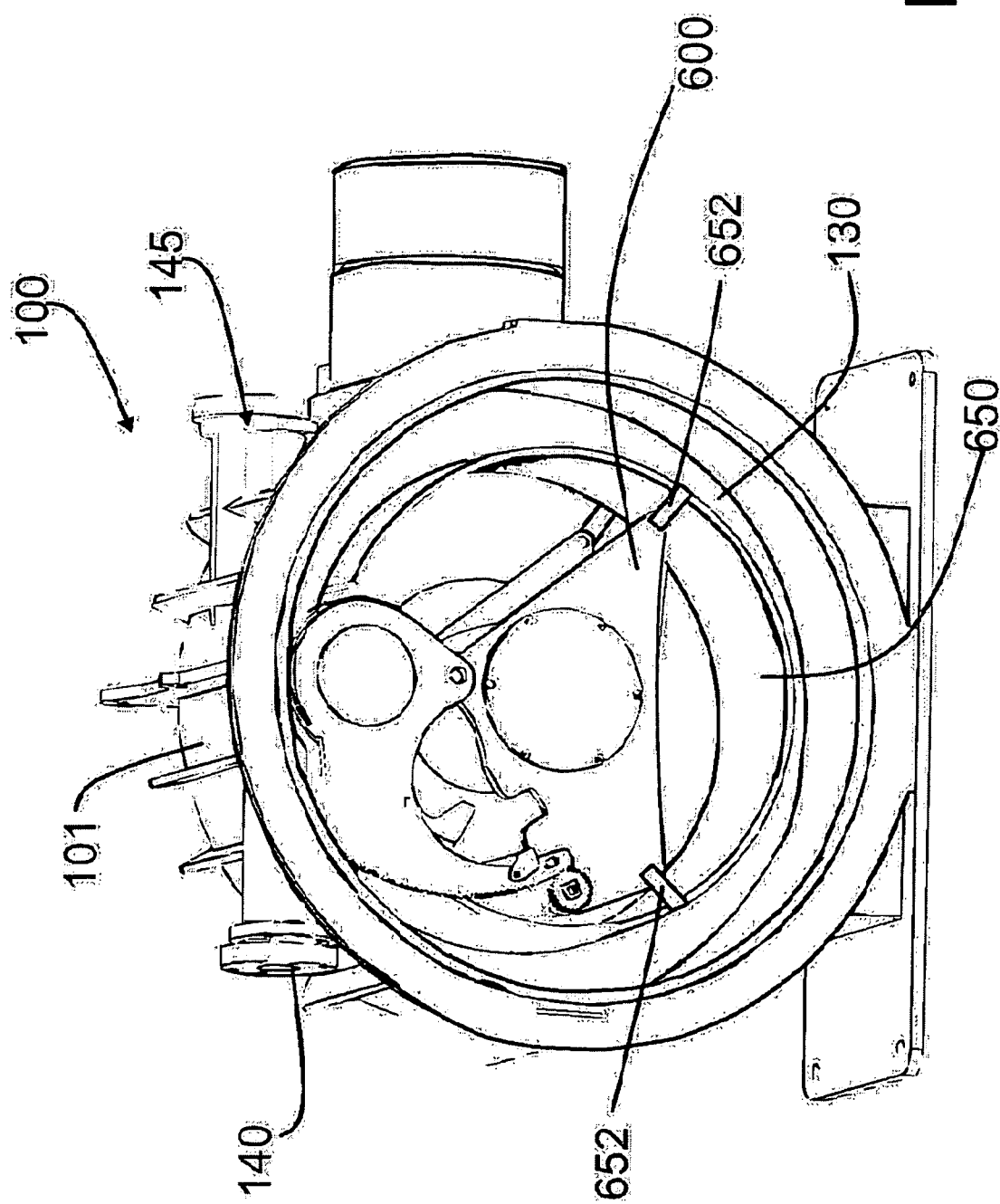
FIG. 2 illustrates an example of a peristaltic pump comprising sliding guide for supporting a hose.

The present solution provides a different kind of supporting element, which supports the hose 130 thoroughly but which is easier to implement within the pump cavity than numerous amount of supporting rollers. FIG. 2 represents a peristaltic pump 100 having an adjustment mechanism as shown in FIG. 1. Instead of supporting rollers, the pump of FIG. 2 comprises a sliding guide 650 for supporting the hose 130. The sliding guide 650 is a mangled sheet (made of steel, plastics, etc.) that is placed in the pump cavity so that the hose 130 is located between the sliding guide 650 and the interior perimeter of the pump cavity. In other words, the sliding guide is arranged between the assembly 600 and the hose 130 to support all such length of the hose 130, which is not in contact with the rotor (FIG. 4: 112). The sliding guide 650 can be fixed to the sleigh 600 by clamps 652 or other type of fasteners. The sliding guide 650 is thus configured to rotate with the sleigh 600 in a sliding manner so that the hose 130 is being supported by the whole round.

Figure 3:
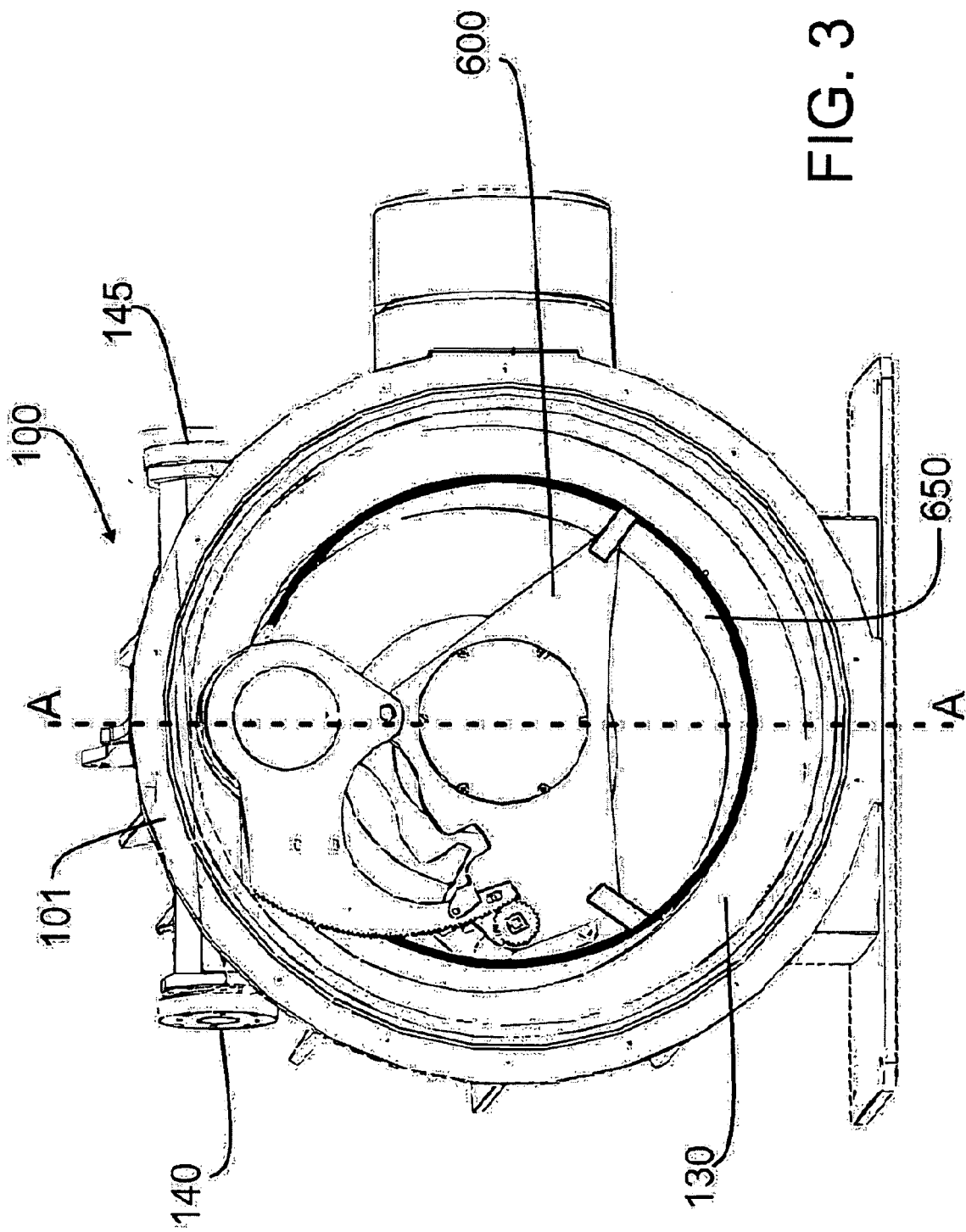
FIG. 3 illustrates another example of a peristaltic pump comprising a sliding guide for supporting a hose with section A-A.

FIG. 3 presents another view of a peristaltic pump 100 comprising a sliding guide 650 for supporting the hose 130. Section A-A is illustrated in FIG. 4 for more detailed discussion.

FIG. 4 shows a view of the section A-A for the peristaltic hose pump 100 comprising supporting means 650 for supporting the hose 130 within the pump body 101. From FIG. 4 it is possible to see the rotor 112 pressing the hose 130. The hose 130 travels within the pump body 101 and is supported by the sliding guide 650. The width "Ws" of the sliding guide 650 should at least equal with the diameter "D" of the hose, but is preferably greater (e.g. twice as wide or more) than the diameter of the hose. However, the width "Ws" of the sliding guide 650 should not exceed the width "Wi" of the inner perimeter 102 of the pump body 101. The sliding guide 650 can be easily arranged within pump cavity of different sizes (e.g. height of the pump can be from 500 mm upwards). Pumps having a height less than 500 mm, can also utilize the principles of the present solution, however an additional attention should be paid to the construction of elements.

FIG. 5 illustrates the sleigh 600 for the peristaltic pump. In use, the sleigh 600 is placed in the cavity of the peristaltic pump. The sleigh comprises at least a rotor, the end 601 of which is shown in FIG. 5, a gear unit 604 and a counterpart 605 for the gear unit. As said, the gear unit 604 can be formed of two gears, at least one gear being located on each end of a shaft of the gear unit 604. The counterpart 605 can be formed corresponding counterpart pieces, between which the rotor can be installed. Therefore at least one counterpart piece (i.e. number corresponding the amount of gears in the gear unit) is located on each end of the rotor. In this example, there are one gear located on each end of the shaft of the gear unit, and one counterpart piece being located on each end of the rotor. However, the need for having more than one gears on each end of the shaft may raise with massive pumps, where e.g. two parallel gears on each end of the shaft are needed. The sliding guide can be fixed to the sleigh 600 by points 602.

The counterpart 605 can be locked to the gear unit 604 by means of a locking means, such as a locking bar 607, for example, that is movable from a locking position (shown in FIG. 5) to a rest position. In the locking position rotor's (the end of which is shown by 601) distance from the inner wall of the pump cavity is the smallest and the compression force applied to the hose is the greatest. In order to enlarge the distance between the rotor (the end of which is shown by 601) and the inner wall of the pump cavity, the position of the locking bar 607 is moved to the rest position, whereby the counterpart 605 is released. In the rest position of the locking bar 607, the gear unit's counterpart 605 is released from the operating position. By this, the gear unit 604 can be rotated, which—in turn—turns the counterpart 605 thus effecting to the rotor's location with respect to the inner wall of the peristaltic pump also. By rotating the gear unit 604 (e.g. with help of a crank or similar), the counterpart 605 can be rotated towards the crankshaft. The counterpart 605 can be rotated as much as is needed for adjusting the distance between the rotor (end of which is referred with 601) and the inner wall of the pump cavity. The distance can be adjusted according to the pump's output pressure (e.g. 0-16 bar or different) for the substance within the hose. In this embodiment, the sleigh comprises one central unit 603, one gear unit 604, one counterpart 605 and one rotor (the end of which is shown with 601). However, other embodiments can comprise two gear units 604, two counterparts 605 and two rotors being coupled to one central unit 603.

In the previous, a supporting element for supporting the hose in the peristaltic pump has been disclosed. The present invention is not limited to the above-described embodiment, but may be varied according to the appended claims.

The sliding guide represents easier, simpler and more reliable supporting solution for peristaltic pumps than e.g. supporting rollers. The invention is characterized by the adjustment mechanism that comprises at least of a gear unit and a counterpart for said gear unit, said counterpart being operatively coupled to said rotor, wherein the gear unit in cooperation with the counterpart are configured to adjust a gap between the rotor outer surface and the pump cavity inner perimeter, and that the assembly is fixed to a sliding guide, said sliding guide being configured to support the hose/tube.

The invention claimed is:
1. A peristaltic pump comprising an assembly comprising:
   a rotor configured to compress a hose being positioned on an inner perimeter of a pump cavity, and
   an adjustment mechanism configured to adjust a compression force imposed on the hose,
   wherein:
   the assembly is coupled to a crankshaft of a pump body,
   the adjustment mechanism comprises a gear unit and a counterpart for the gear unit,
   the counterpart is operatively coupled to the rotor, the gear unit in cooperation with the counterpart is configured to adjust a gap between an outer surface of the rotor and the inner perimeter of the pump cavity, the assembly is fixed to a sliding guide that is configured to support a portion of the hose that is not in contact with the outer surface of the rotor, the gear unit comprises a shaft and a gear on each end of the shaft, and the counterpart for the gear unit comprises a counterpart piece on each end of a shaft of the rotor.

2. The peristaltic pump according to claim 1, wherein bearings of the crankshaft are arranged within the pump cavity.

3. The peristaltic pump according to claim 1, further comprising a locking means configured to function in a locking position and a rest position, wherein:
- the locking means in the locking position is configured to lock the adjustment mechanism, and
- the locking means in the rest position is configured to enable an adjusting operation of the adjusting mechanism.

4. The peristaltic pump according to claim 1, wherein the gear unit is rotatable with a crank.

\* \* \* \* \*